US008894679B2

(12) United States Patent
Begg

(10) Patent No.: US 8,894,679 B2
(45) Date of Patent: Nov. 25, 2014

(54) SURGICAL PUNCTURE ACCESS WITH PRELOAD LOCK

(71) Applicant: Massachusetts Institute of Technology, Cambridge, MA (US)

(72) Inventor: Nikolai David Michael Begg, Wellesley, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/673,224

(22) Filed: Nov. 9, 2012

(65) Prior Publication Data

US 2014/0135704 A1    May 15, 2014

(51) Int. Cl.
*A61B 17/34* (2006.01)
*A61M 5/178* (2006.01)

(52) U.S. Cl.
CPC .................................. *A61B 17/3468* (2013.01)
USPC .................. 606/185; 604/164.12; 604/165.01

(58) Field of Classification Search
USPC .................. 604/165.01, 165.02, 506, 164.01, 604/164.06, 164.12; 606/182–185
See application file for complete search history.

(56) References Cited

U.S. PATENT DOCUMENTS

| 4,535,773 | A |  | 8/1985 | Yoon |  |
|---|---|---|---|---|---|
| 5,053,010 | A |  | 10/1991 | McGary et al. |  |
| 5,211,629 | A |  | 5/1993 | Pressly et al. |  |
| 5,320,610 | A |  | 6/1994 | Yoon |  |
| 5,336,176 | A |  | 8/1994 | Yoon |  |
| 5,514,111 | A |  | 5/1996 | Phelps |  |
| 5,632,733 | A |  | 5/1997 | Shaw |  |
| 5,851,216 | A | * | 12/1998 | Allen | ........................... 606/185 |
| 6,090,077 | A |  | 7/2000 | Shaw |  |
| 7,351,224 | B1 |  | 4/2008 | Shaw |  |
| 7,927,303 | B2 |  | 4/2011 | Wyrick |  |
| 2006/0173480 | A1 |  | 8/2006 | Zhang |  |
| 2011/0130744 | A1 |  | 6/2011 | Kassab et al. |  |

OTHER PUBLICATIONS

Loschak, Paul et al., "Cranial Drilling Tool with Retracting Drill Bit Upon Skull Penetration", biorobotics.harvard.edu/pubs/2012/contrib/DMD2012_Loschak NPL-49 Aug. 4, 2012 , 1 page.
"International Application Serial No. PCT/US2012/048221, Search Report and Written Opinion mailed Oct. 16, 2012", PCTUS2012048221-ISR-101612 NPL-48, 6 pages.

* cited by examiner

*Primary Examiner* — Nicholas Lucchesi
*Assistant Examiner* — Leah Stohr
(74) *Attorney, Agent, or Firm* — Strategic Patents, P.C.

(57) ABSTRACT

A surgical device mitigates over-puncture with a bias spring that biases a leading, cutting edge in the opposite direction of the anticipated over-puncture. An associated locking mechanism is configured to release the force of the bias spring in a direction counter to the direction of insertion when the tension force of tissue against the cutting edge is released. Thus, when an opening in the tissue forms, the tension is released and the cutting edge can move opposite to the direction of insertion of the surgical device at the same time that an applied force drives the instrument in the direction of insertion. In this manner, the spring and locking mechanism cooperate to move the cutting edge opposite to the direction of insertion as soon as an incision is made.

15 Claims, 17 Drawing Sheets

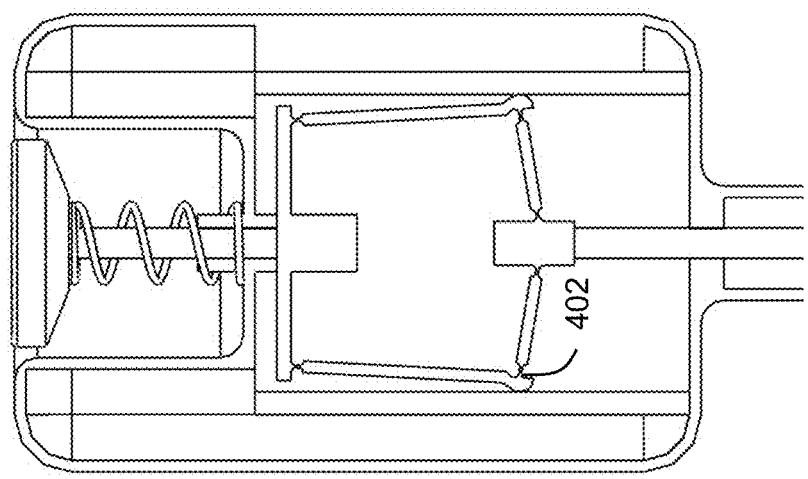
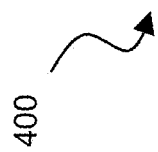
Fig. 4

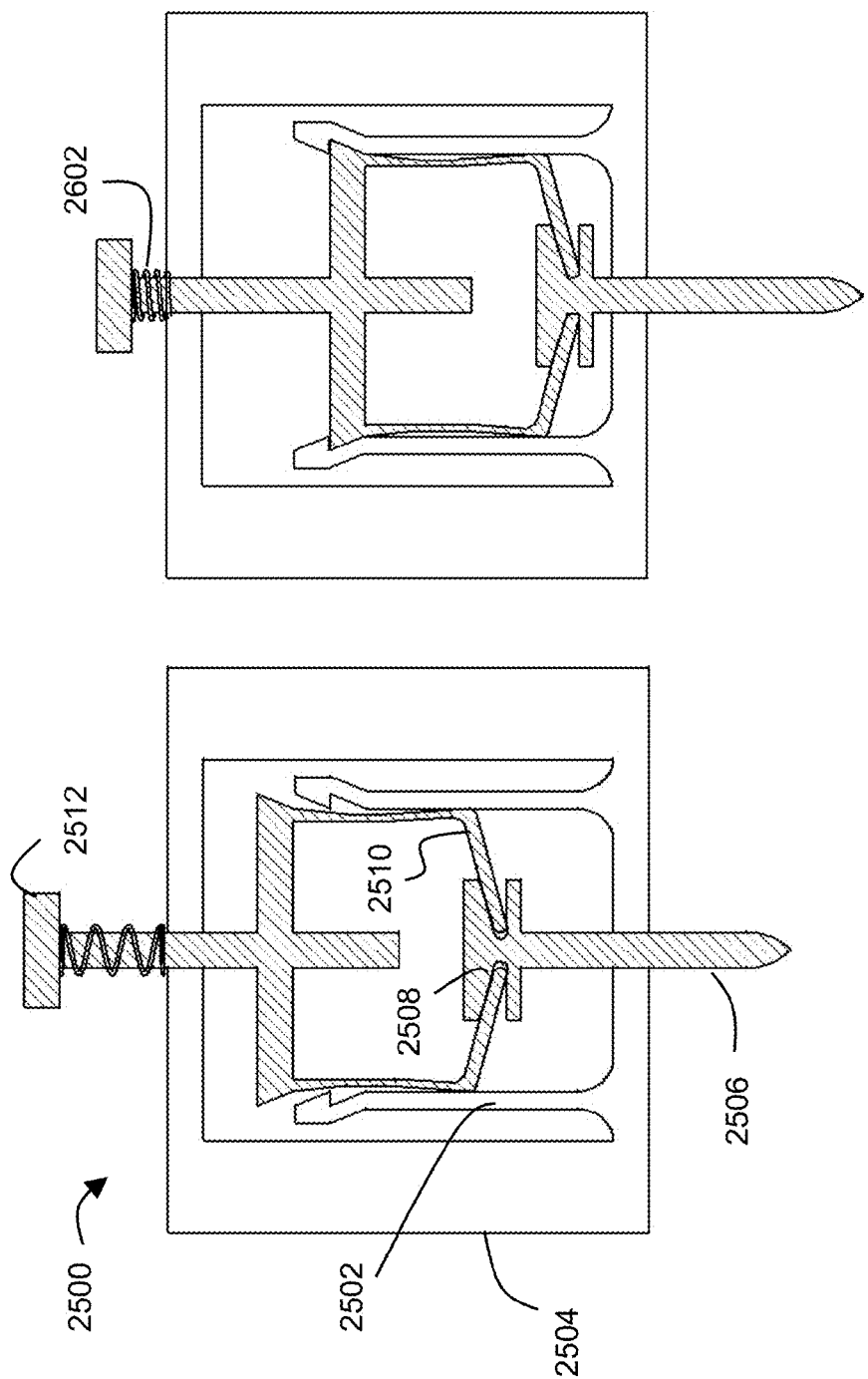

SURGICAL PUNCTURE ACCESS WITH PRELOAD LOCK

BACKGROUND

In minimally invasive surgical procedures, one or more tissue layers must sometimes be punctured without direct visualization of an instrument tip in order to gain access to a body cavity, duct, or the like. The instruments for such procedures are generally long and slender with high axial stiffness. In use, a surgeon or other user applies sufficient axial force so that the instrument can penetrate into the tissue by cutting, tearing or separating tissue fibers.

At the point of puncture, or the instant when the tissue opens at the tip of the instrument, the force applied to the instrument by tissue tension goes to zero while the force applied by the user remains as a net force accelerating the instrument into the surgical site. Device designers have attempted to improve instruments to mitigate this forward driving force and subsequent acceleration by offering dynamic blade covers, blunt-tipped devices, and other features that indirectly address the problem of over-puncture by seeking to reduce the harmful effects when an over-puncture occurs.

There remains a need for puncture devices that reduce or eliminate the over-puncture event, rather than addressing consequences of an over-puncture after it occurs. There remains a further need for a puncture device that locks in a preloaded state for improved ease of use.

SUMMARY

A puncture device mitigates over-puncture with a bias spring that biases a leading, cutting edge in the opposite direction of an anticipated over-puncture. An associated locking mechanism is configured to release the force of the bias spring when a puncture event releases the tension force of a target surface such as tissue against the cutting edge. A preload lock secures the cutting edge in a loaded state until an initial engagement with the target surface. When the cutting edge initially engages tissue with an applied force, the preload lock releases, and when an opening in the tissue forms, the locking mechanism for the cutting edge also releases so that the cutting edge can move opposite to the direction of puncture at the same time that an applied force drives the instrument in the direction of insertion. In this manner, the spring and locking mechanism cooperate to move the cutting edge opposite to the direction of insertion as soon as an incision is made.

DRAWINGS

The invention may be more fully understood with reference to the accompanying drawings wherein:

FIG. 4 is a cross-sectional view of a device for surgical puncture access.

FIG. 25 illustrates a puncture device with a preload lock.

FIG. 26 illustrates the puncture device of FIG. 25 in a preloaded state.

DETAILED DESCRIPTION

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus the term "or" should generally be understood to mean "and/or" and so forth.

Disclosed herein are systems and methods for surgical puncture access, and in particular, puncture access using a retraction mechanism that retracts a blade in a direction opposite to a puncture force when a puncture is achieved and the resistive force of intervening tissue is removed. Although the disclosed retraction mechanisms are intended for a trocar in a surgical procedure, the principles of the invention have wide applicability. In a surgical context, any puncture-access device may employ similar techniques to prevent over-puncture, including a Veress needle, a venous access needle for catheter placement, an epidural or spinal tap needle, a cranial drill, and a lung puncture device to correct a collapsed lung.

More generally, the phenomenon of over-puncture appears in areas outside medicine and the principles of the invention may be applied in numerous non-medical contexts. For example, in certain manufacturing processes, a hole is drilled through a wall or vehicle body behind which lies a pipe, electrical conduit, gas tank, or other fragile or dangerous object. A power drill may be adapted to use the principles of the invention in order to drill only through the wall and no further, retracting a drill bit or the like when a complete puncture has been achieved. In similar fashion, a drill press can be adapted to prevent a user from drilling through a part and into a drilling table or chuck. Much larger industrial drilling applications through rock or soil could similarly benefit from these mechanisms to prevent damage due to over-drilling. All such variations that would be apparent to one of ordinary skill in the art are intended to fall within the scope of this disclosure.

Figure 1:
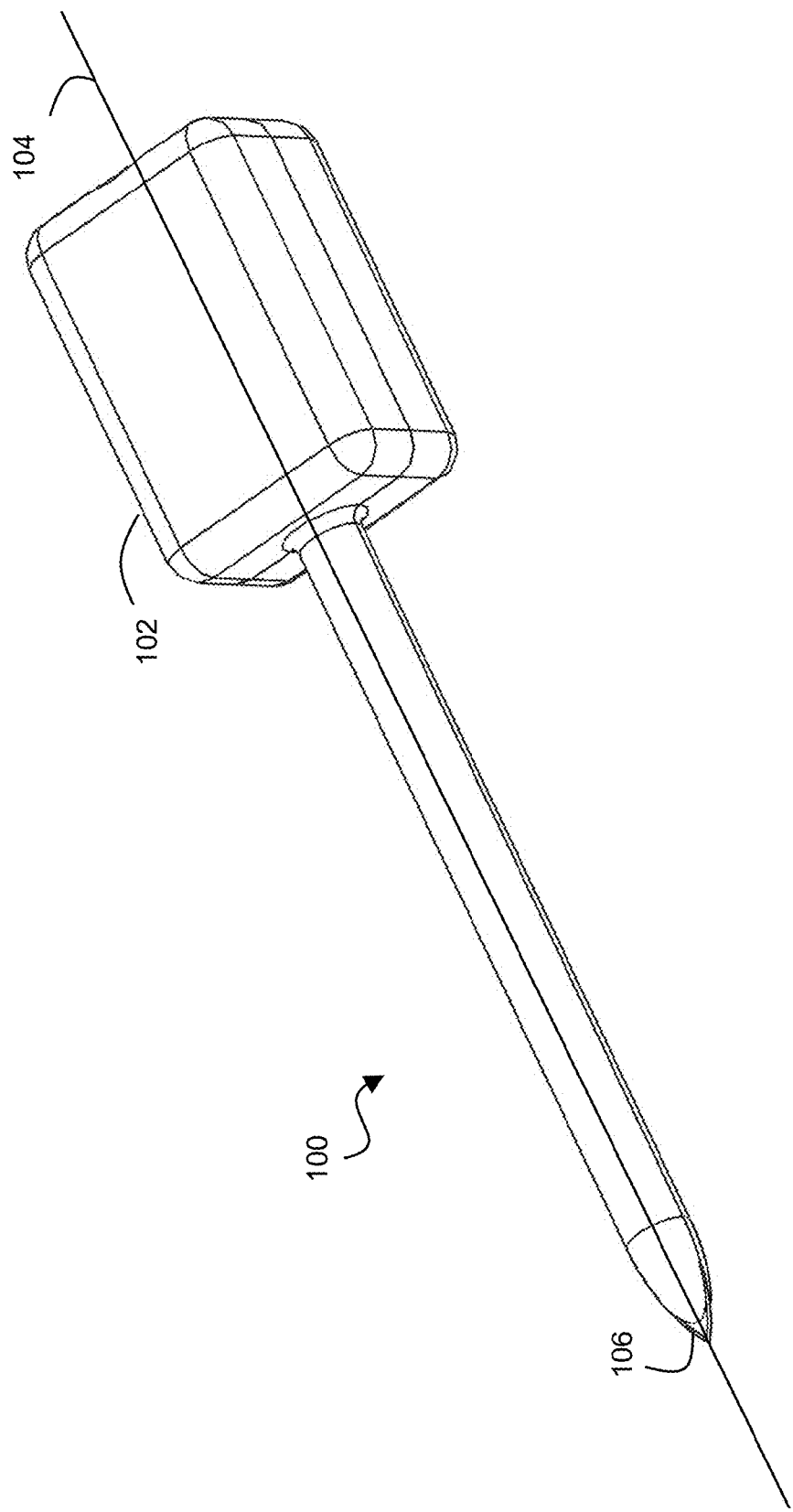
FIG. 1 is a perspective view of a device for surgical puncture access.

FIG. 1 is a perspective view of a device for surgical puncture access. In general, the device 100 may include a housing 102 with an axis 104 oriented through the housing 102 in a direction of applied force as described below. As depicted, the device 100 is in a deployed position where a functional tip 106 of an instrument such as a cutting edge of a surgical blade extends outside the housing where it can be used in a cutting procedure or the like.

Figure 2:
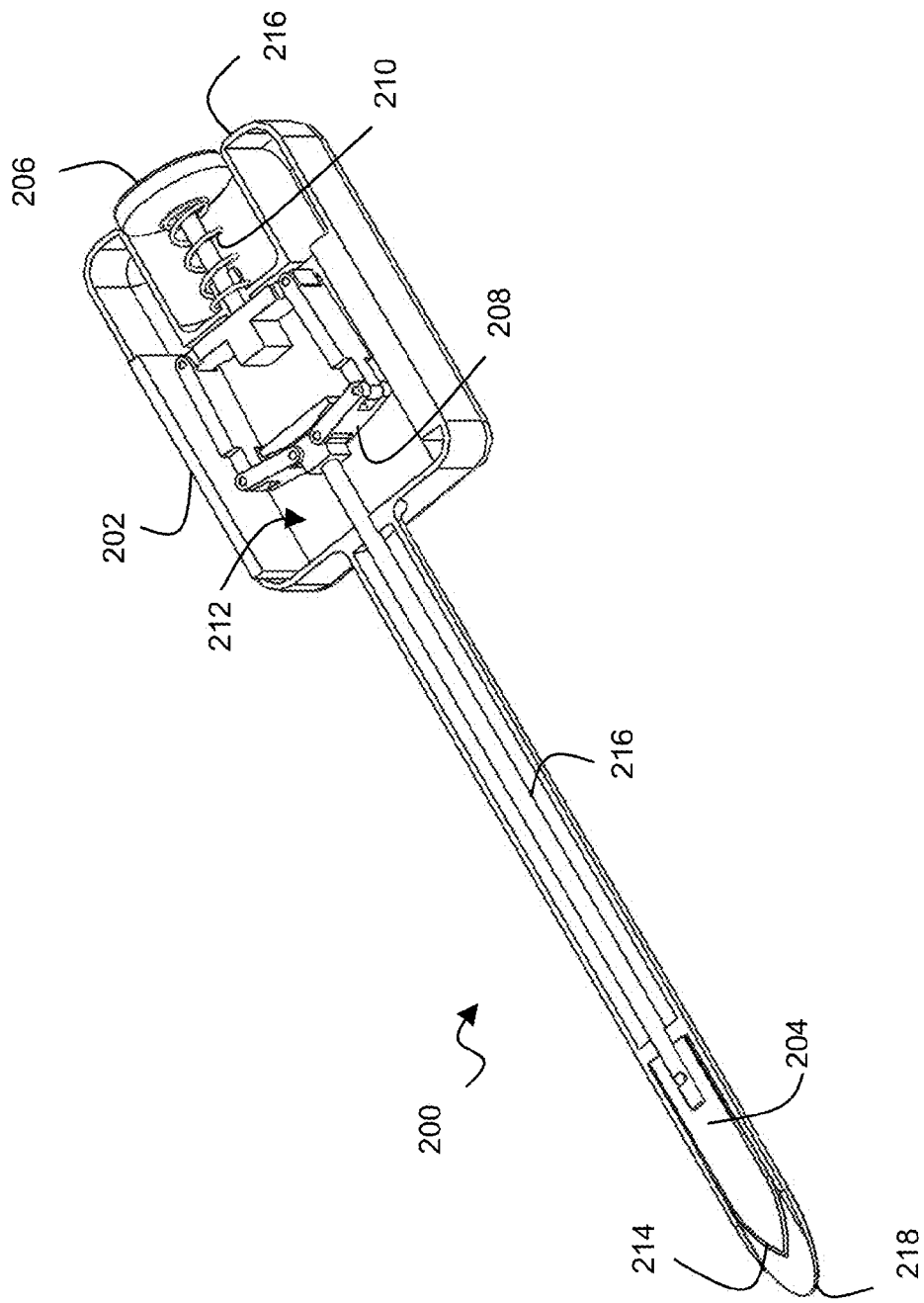
FIG. 2 is a cut-away perspective view of a device for surgical puncture access.

FIG. 2 is a cut-away perspective view of a device for surgical puncture access. In general, the device 200, which may be the device 100 described above, may include a housing 202, an instrument 204, a mechanical control 206, a locking mechanism 208, and a biasing mechanism 210.

The housing 202 may be formed of any suitable material such as biocompatible plastic or surgical stainless steel, and may enclose various components of the device 200. The housing 202 may be a trocar shaped and sized for use in a laparoscopic procedure. More generally, the housing 202 may be of any other shape and size suitable for a particular medical or industrial application as contemplated herein. The housing has an interior 212 that contains various components of the device 200.

The instrument 204 may be slideably retained within the housing so that it can move axially (i.e., along the axis 104 depicted in FIG. 1) during use. More specifically, the instrument 204 may be slideably retained within the housing 202 and movable along the axis between a first position where a functional tip of the instrument 204 extends outside the housing 202 (as depicted in FIG. 1) and a second position where the functional tip rests within the housing 202 (as depicted in FIG. 2).

The instrument 204 may include a blade 214 such as an off-the-shelf symmetrical scalpel blade or any other blade or cutting instrument, or more generally any functional tip such as a drill bit, an awl or other piercing instrument, or the like. The instrument 204 may also include a shaft 216 that mechanically couples the blade 212 to other components of the device 200. The shaft 216 may be coupled to the blade 214 with a pin, dowel, or any other permanent or removable/ replaceable attachment fixture. In FIG. 2, the instrument 204 is depicted in a retracted position where the blade 204 is disposed within the housing 202. In this position, the tip of the blade 214 is shielded within an insertion end 216 of the housing that has a rounded or blunt tip so that the device 200, with the blade 214 in this retracted position does not have an exposed cutting surface. The blade 214 may be fully enclosed by a second half of the housing that is not shown here.

The mechanical control 206 may be coupled (e.g., through the locking mechanism 208) to the instrument 204 and provides a manual control to move the instrument from the second (retracted) position to the first (deployed) position. This may, for example, include a plunger as depicted or any similarly operable device such as a slide or tab on a side of the housing 202 that permits axial movement of the instrument 204 into the deployed position by a user. Thus, the mechanical control 206 may be generally operable at a first end 216 of the housing 202 distal from a second end 218 of the housing 202 where a functional tip of the instrument 204 deploys from the housing 202.

The locking mechanism 208 may be generally configured to secure the instrument against movement toward the second (retracted) position when the instrument is in the first (deployed) position and a force is applied to the blade 214 of the instrument 204 along the axis of the housing 202 and toward the interior 212 of the housing 202, or toward the first end 216 of the housing 202 opposite the second end 216 (the insertion end). The locking mechanism 208 may also release the instrument 204 to move toward the second (retracted) position when the force applied to the blade 214 is removed.

The biasing mechanism 210 generally biases the instrument 204 toward the second position where the instrument 204, or more specifically the blade 214 or other function tip of the instrument is enclosed within the housing 202. The biasing mechanism may, for example, include a coil spring or other spring configuration coupled between the mechanical control 206 (e.g., a plunger) and the housing 202, or any other suitable spring mechanism, elastic mechanism, or the like.

The cooperation of the locking mechanism 208 and the accompanying biasing mechanism 210 is discussed below, and generally facilitates retraction of the instrument 204 in a direction opposite to the direction of puncture when the loading force on the instrument 204 decreases, e.g., after a puncture is achieved.

Figure 3:
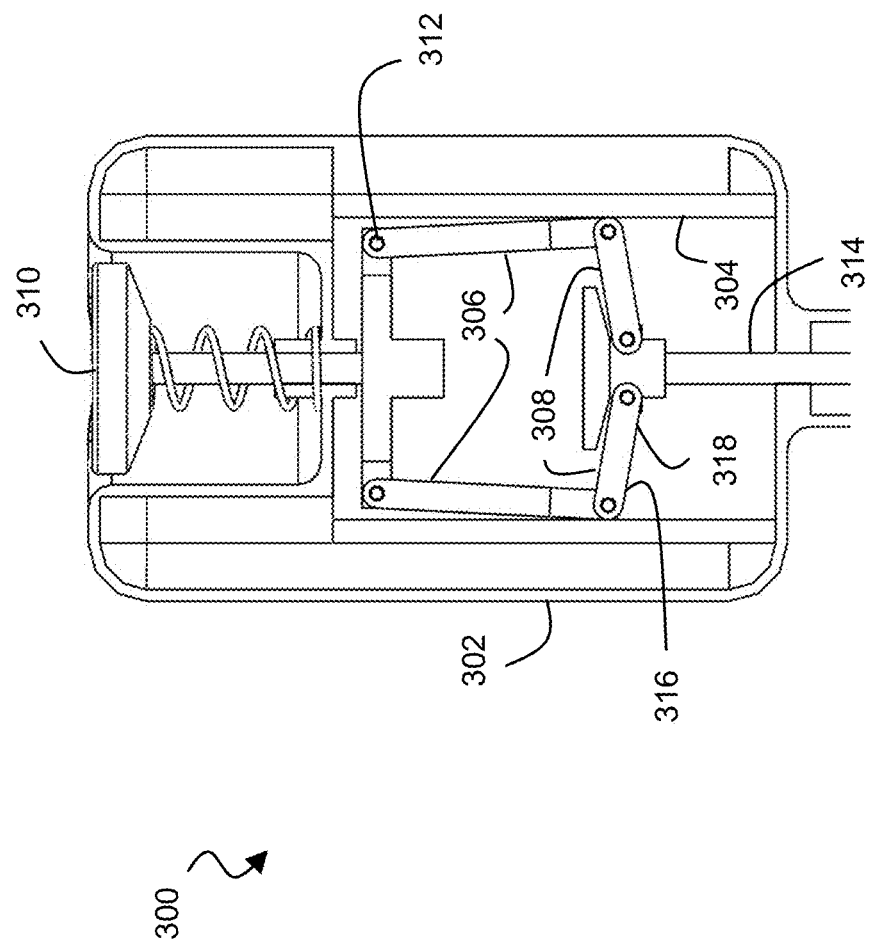
FIG. 3 is a cross-sectional view of a device for surgical puncture access.

FIG. 3 is a cross-sectional view of a device for surgical puncture access. The device 300 may include a housing 302, which may be any of the housings described above, with an interior wall 304. A locking mechanism as described above may be formed of a first plurality of members 306 and a second plurality of members 308.

The first plurality of members 306 may be coupled to a plunger 310 or other mechanical control through a base plate or the like, which may include one or more hinges 312 to permit rotation of the first plurality of members 306 during use. In general, the first plurality of members may be oriented substantially parallel to the interior wall 304 of the housing 302. In this orientation, the plunger 310 can apply a force to move an instrument connected to a shaft 314 from a retracted position inside the housing 302 to a deployed position outside the housing 302. It will be understood that being oriented substantially parallel to the interior wall 304 does not require strict mathematical parallelism. Rather, each of the first plurality of members 306 may be generally closer to parallel than normal, or otherwise oriented sufficiently close to parallel to deliver an axial force from the plunger 310 against a biasing spring or the like to move the shaft 314 forward (or downward, in FIG. 3) and deploy an instrument. By orienting the first plurality of members 306 nearly parallel to the interior wall 304, a force applied to the plunger 310 creates a relatively small normal force against the interior wall 304 and prevents the locking mechanism from locking by friction against the interior wall 304 of the housing.

The second plurality of members 306 may be hingeably coupled on a first end 316 to the first plurality of members, and coupled to the instrument (e.g., through the shaft 314) on a second end 318. The second plurality of members 306 may be oriented substantially normal to the interior wall 304 of the housing. In this orientation, the first end 316 of each of the second plurality of members 306 can apply a normal force to frictionally engage the interior wall 304 of the housing 302 in a non-sliding mechanical relationship when a load is applied to the blade or other functional tip of an instrument coupled to the shaft 314. More specifically a force applied in a direction from the deployed position to the retracted position along the axis of the housing 302 is converted through the linkages of the locking mechanism into a relatively large normal force into the interior wall 304 at the ends 316 of the second plurality of members 308.

For the second plurality of members 308, being oriented substantially normal to the interior wall 304 does not require strict mathematical orthogonality. Rather, each of the second plurality of members 308 may be generally closer to normal than parallel, or otherwise oriented sufficiently close to normal to deliver a normal force to the interior wall 304 so that the first end 316 of each of the second plurality of members 308 can frictionally engage the interior wall 304 and secure the shaft 314 against further movement toward a retracted position. This arrangement advantageously increases the locking effect of the frictional engagement as the retraction load on the shaft 314 increases.

In operation, the locking mechanism may secure an instrument against moving from a first position outside the housing 302 to a second position within the housing 302 by frictionally engaging the interior wall 304 of the housing 302 with a force proportional to a load applied to the functional tip in a direction from the first position to the second position along the axis of the housing 302. When the load is removed, the complementary normal forces against the interior wall 304 are similarly removed, and the spring or other biasing mechanism can return the instrument to the second (retracted) position.

It will be understood that while two pairs of members are shown, any number of members may be used. For example, the locking mechanism may use three or more pairs of members in a radial configuration within a cylindrical housing interior. Similarly, the principles of the locking mechanism may be usefully adapted to employ a single first and second member in an asymmetrical configuration. Thus, the arrangement of components in the locking mechanism of FIG. 3 is provided by way of example only, and is not intended to limit the scope of the invention.

FIG. 4 is a cross-sectional view of a device for surgical puncture access. In an alternative configuration of the device 400, the first and second plurality of members may be formed of a monolithic piece of material with flexural hinges 402 such as corner-filleted hinging elements in place of the pin-based hinge elements depicted in FIG. 3. Operation of this device 400 is otherwise similar to the device 300 depicted in FIG. 3.

Figure 5:
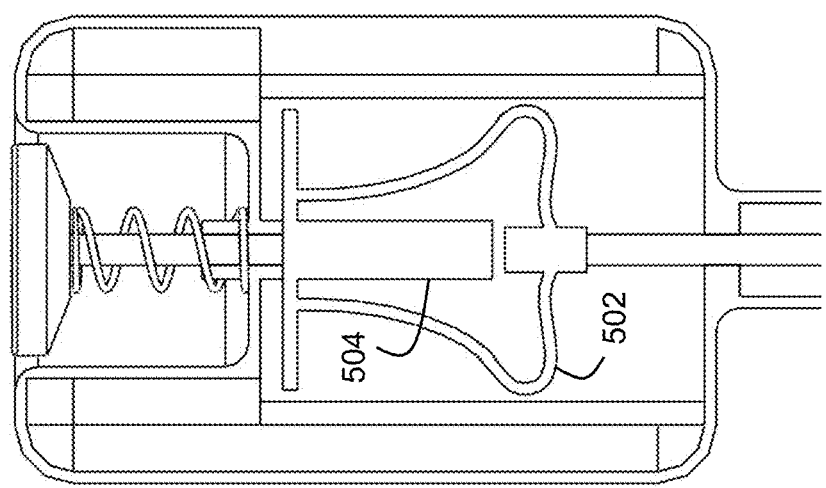
FIG. 5 is a cross-sectional view of a device for surgical puncture access.

FIG. 5 is a cross-sectional view of a device for surgical puncture access. In an alternative configuration of the device 500, the locking mechanism may be formed of curved elements 502 that generally reproduce the loading schemes discussed above without use of hinges or discrete structural members.

The device 500 may include a mechanical stop 504 positioned to prevent collapse of the locking mechanism and comprise of the locking function under large loads. In general, the mechanical stop 504 prevents a lower portion of the integral locking mechanism—that portion that extends substantially normal to the interior wall of the housing—from moving past a normal or ninety degree orientation where further displacement of the shaft will not provide additional frictional force against the interior wall. It will be appreciated that the mechanical stop 504 may be usefully incorporated into any of the embodiments described above. For example, in the embodiment of FIG. 3, the mechanical stop 504 may be positioned to prevent the second plurality of members from hinging beyond a predetermined angle relative to the interior wall of the housing, such as beyond ninety degrees where increased force would no longer yield increased frictional loading against the interior wall.

Operation of a surgical puncture access device is now described in greater detail with reference to a puncture operation.

Figure 6:
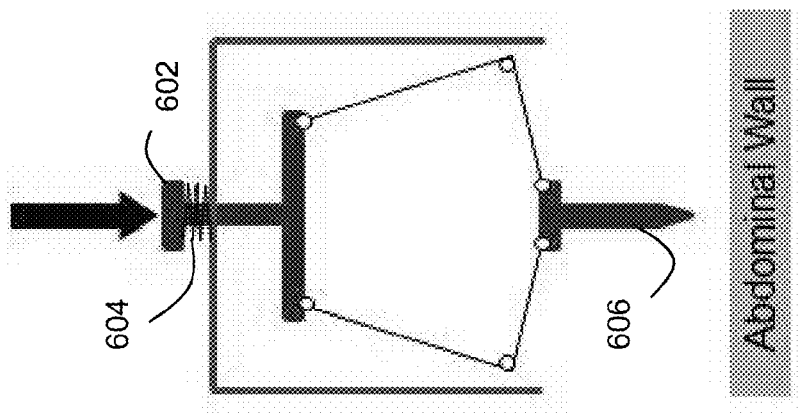
FIG. 6 depicts spring loading of a device.

FIG. 6 depicts spring loading of a device. In an initial step, a plunger 602 or other mechanical control is depressed to create a bias force against a spring 604. In this state, a functional tip 606 is deployed, but there is no force independent of the plunger 602 maintaining the functional tip 606 in this position.

Figure 7:
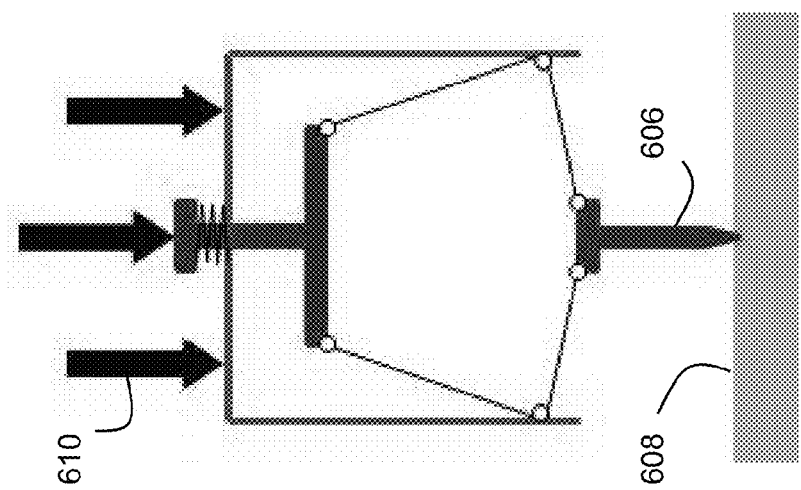
FIG. 7 depicts locking of a spring-loaded device.

FIG. 7 depicts locking of a spring-loaded device. In this step, the device is pressed against a target surface such as an abdominal wall 608 of a surgical patient. Thus the force applied to the functional tip 606 may be created by applying an axial force to the housing of the device (as indicated by arrows 610) while the cutting edge or other functional tip 606 engages a tissue layer of a patient. While an abdominal wall 608 is depicted, it will be understood that this tissue layer may also or instead include skin, muscle, peritoneum, or any other superficial layer of tissue, depending on whether and to what extent skin and other layers are surgically exposed prior to use of the device. The axial force may be obtained by a user gripping the device in any suitable manner and applying an axial load toward the target surface. It will be noted that at the moment of engagement with the target surface, two complementary forces—a first force applied to the plunger and a second force applied to the functional tip 606—are used to secure the instrument in the deployed position. These two complementary forces create the outward or normal force on the interior wall of the housing that frictionally engages the locking mechanism. However, once so engaged, the force on the functional tip 606 can sustain the locking effect and the force applied to the plunger may be removed, thus permitting free manipulation of the housing by a user, provided that the functional tip 606 remains forcibly engaged with the target surface.

Figure 8:
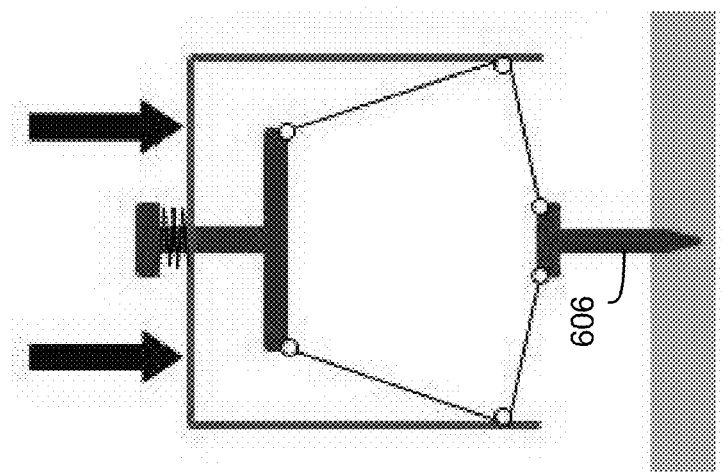
FIG. 8 depicts initiation of a puncture with a spring-loaded device.

FIG. 8 depicts initiation of a puncture with a spring-loaded device. In this step, the housing may be manually driven into the target surface so that the cutting edge of the instrument can puncture the surface. The force manually applied to the housing is directly translated to the functional tip 606 to obtain this cutting action.

Figure 9:
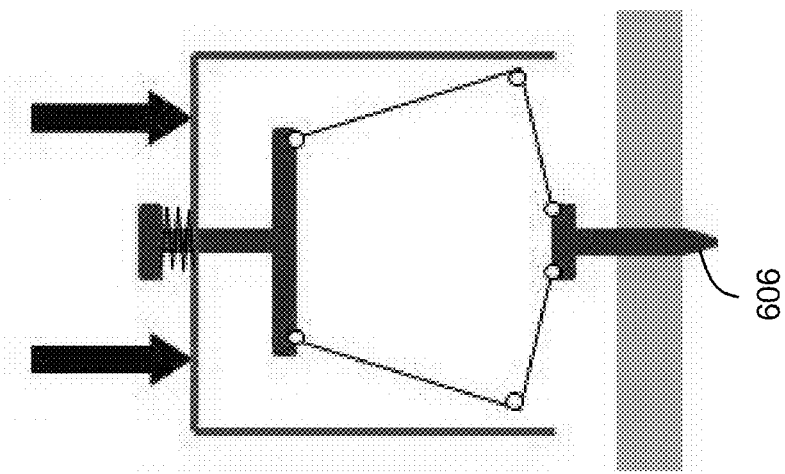
FIG. 9 depicts completion of a puncture with a spring-loaded device.

FIG. 9 depicts completion of a puncture with a spring-loaded device. In this step, the functional tip 606 has been driven through the surface. When the cutting edge of the functional tip 606 punctures the target surface (e.g., peritoneum of a patient), the force against the functional tip 606 is removed, and so is the resulting normal force against the housing. Without this normal force to secure frictional engagement with the housing, the locking mechanism can separate from the interior wall of the housing. This is illustrated as a small gap between the locking mechanism and the interior wall of the housing, however, physical separation of the surfaces is not required. The desired reduction in frictional engagement may be achieved while the two surfaces remain in contact, albeit under a reduced normal force.

Figure 10:
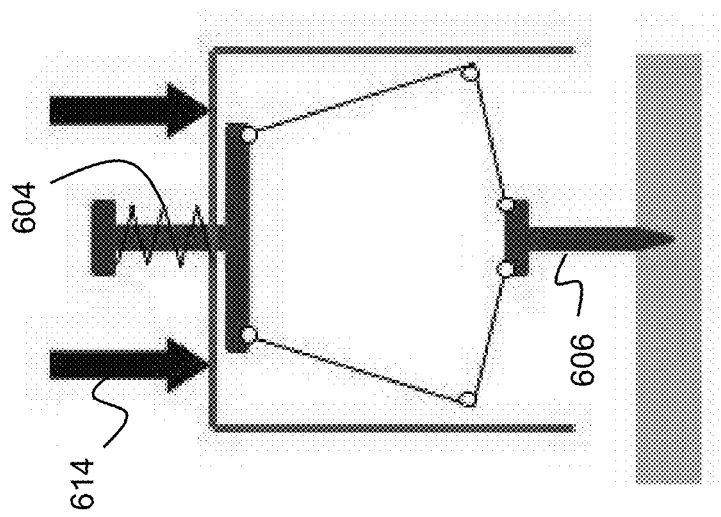
FIG. 10 depicts retraction of a blade of spring-loaded device.

FIG. 10 depicts retraction of a blade of spring-loaded device. When the frictional engagement of the locking mechanism to the interior wall is reduced or removed, the spring 604 can operate to retract the functional tip 606 in a direction opposite to the driving force 614 on the housing, thereby retracting the functional tip 606 at the moment of puncture and mitigating the over-puncture event.

Figure 11:
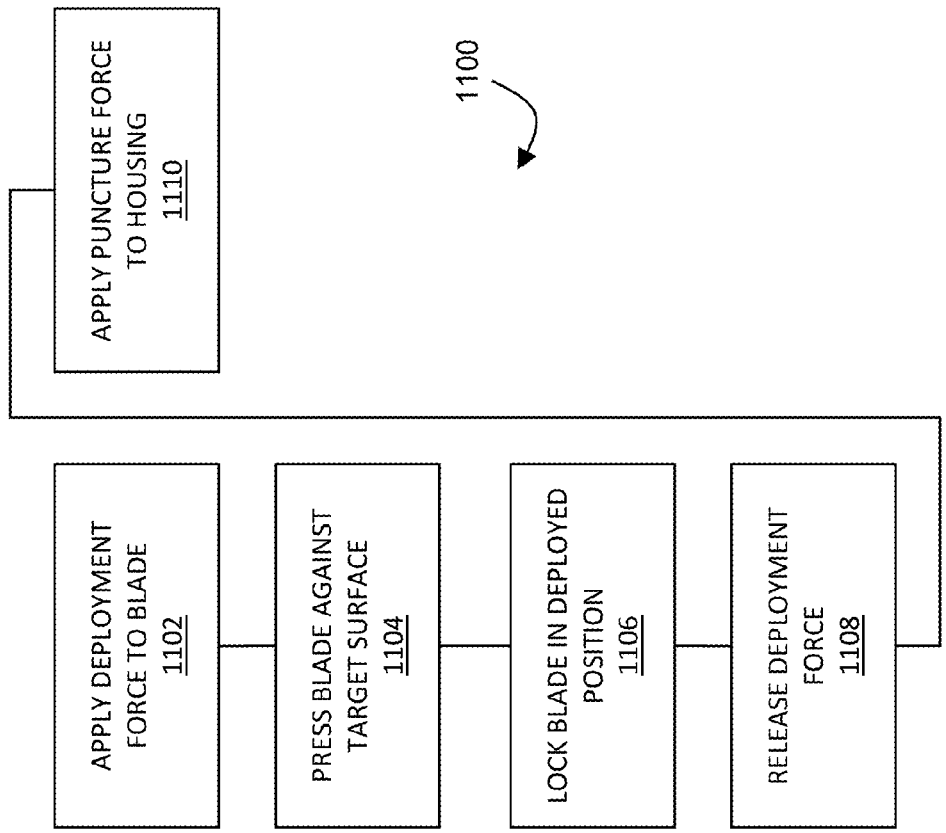
FIG. 11 is a flow chart of a method for surgical puncture access.

FIG. 11 is a flow chart of a method for surgical puncture access. The method 1100 may be performed using any of the devices described above.

As shown in step 1102, the method 1100 may begin with applying a deployment force to spring load a blade in a deployed position exposed outside a housing with a bias to return to a retracted position within the housing. This may for example include depressing a plunger or other control mechanism on the housing of the device. The bias may be achieved for example with a coil spring or any other suitable spring or elastic mechanism, or any combination of the foregoing that can provide sufficient biasing force to retract the blade or other functional tip as contemplated herein.

As shown in step 1104, the method 1100 may include pressing the blade against a target surface while in the deployed position, thereby creating a force against the blade.

As shown in step 1106, the method 1100 may include locking the blade in the deployed position by directing the force against the blade normally against an interior wall of the housing to establish a friction fit proportional to the force. This locking step is performed mechanically by the components of the device in response to the user-controlled steps of spring loading as in step 1102 and engagement with a target surface as in step 1104.

As shown in step 1108, the method may include releasing the deployment force on the plunger or other control mechanism. With the locking obtained in step 1106 and sustained force of the blade against a target surface, the blade can remain locked in the deployed position notwithstanding a driving force (e.g., by the hand of a user) of the housing and blade into the target surface. Thus, the hands of a user are free to manipulate the deployed blade to obtain a puncture of the target surface in any desire manner.

As shown in step 1110, a puncture force may be applied to the housing. This puncture force, which may be any suitable surgical puncture action or technique that maintains a force of the blade against the target surface, may drive the blade through the target surface. As a result, the force against the blade is released and the bias in the spring or other biasing mechanism can withdraw the blade into the retracted position. A similar effect may be achieved by simply removing the blade from the target surface, which would also remove the force against the blade, release the locking mechanism, and cause the spring to retract the blade into the housing. In order to resume the procedure from this state, the blade can once again be deployed with a deployment force as described in step 1102 and the method 1100 may be repeated.

A surgical puncture access tool as described above may in general be improved by a preload lock that secures a blade or other functional tip in a deployed position until ready for use. This may simplify operation of the tool so that the device can be preloaded, e.g., with a plunger or the like, and then pressed against a target surface for application of a puncture force. The axial force from initially pressing the tool against the target surface may first release the preload lock so that the tool is in a state as generally described above for application of a puncture force. Systems and methods for preload locking are now described in greater detail.

Figure 12:
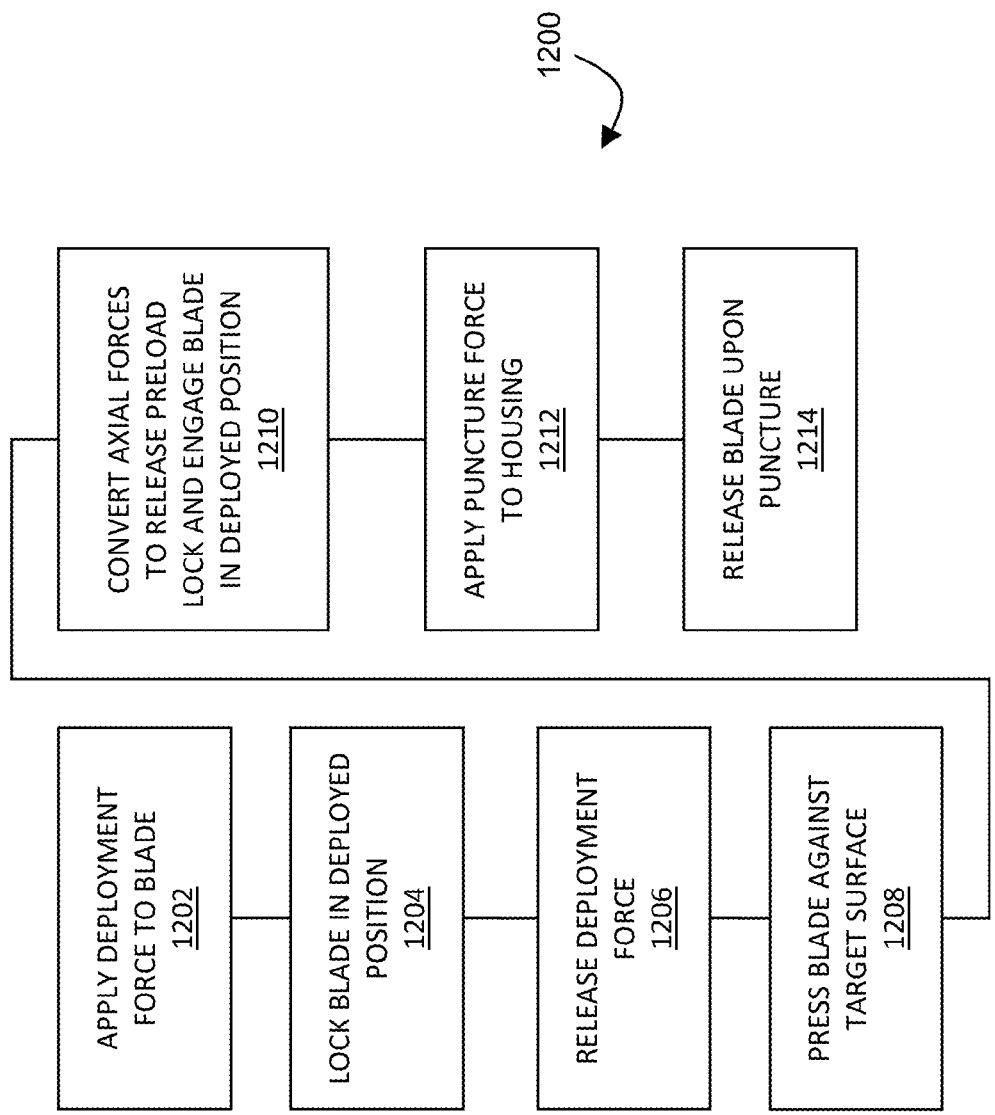
FIG. 12 is a flowchart of a method for puncture access with a tool that provides preload locking.

FIG. 12 is a flowchart of a method for puncture access with a tool that provides preload locking. In general, a preload lock secures a tool in a deployed position with a preloaded bias force to retract a functional tip upon subsequent occurrence of a puncture event. It will be appreciated that while the following method 1200 is described with reference to a blade, the method may be readily adapted to any instrument with a functional tip (e.g., a drill or an awl) that is used with a puncture force.

As shown in step 1202, the method 1200 may begin with applying a deployment force to spring load a blade in a deployed position exposed outside a housing with a bias to return to a retracted position within the housing. This may for example include depressing a plunger or other control mechanism on the housing of the device to move the blade from a first position within the housing to a second, deployed position extending from the housing. The bias may be achieved for example with a coil spring, flexural spring element, or any other suitable spring, elastic or other compliance mechanism, or any combination of the foregoing that can provide sufficient biasing force to retract the blade or other functional tip as contemplated herein.

As shown in step 1204, the method 1200 may include locking the blade in the deployed position. This may be accomplished, e.g., by any of the preload locking mechanisms described below. In this preloaded state, the blade is deployed in a position protruding from the housing for use in a puncture procedure, and does not require a sustained deployment force to remain in this state. At the same time, the biasing force to return the blade to the retracted position is maintained by the preload lock, which mechanically engages the blade in this deployed, pre-biased position.

As shown in step 1206, the deployment force, e.g., the force applied to a plunger, slider, or the like to deploy the blade, may be released and the device can remain secured in this preloaded state by the preload lock.

As shown in step 1208, the method 1200 may include pressing the blade against a target surface while in the deployed position, thereby creating a force against the blade, e.g., an axial force normal to the target surface and toward the housing.

As shown in step 1210, the method 1200 may include converting the axial force into forces for a number of different functions. In one aspect, the axial force may be converted into a first force to release the preload lock, and the corresponding preload locking force. While this might free the blade to move in response to the biasing force within the device, the axial force may also be converted, e.g., substantially concurrently, into a second force normal to an interior surface of the housing to establish a friction fit against the interior surface proportional to the force against the blade. It will be understood that the second force need not be exclusively normal to the interior surface. Instead, the second force may have any normal component that increases in proportion to the axial loading on the blade such that the blade can be retained in the deployed position under an increasing applied force to achieve a puncture. A variety of mechanisms for providing the first force and second force are described with reference to the figures below.

In general, the second force may be created using mechanisms such as those described above to achieve locking of the blade under sustained force by the blade against the target surface. This locking may maintain the blade in the deployed position notwithstanding a driving force (e.g., by the hand of a user) of the housing and blade into the target surface. Thus, the hands of a user are free to manipulate the deployed blade to obtain a puncture of the target surface in any desire manner, provided that an axial force is maintained on the blade.

As shown in step 1212, a puncture force may be applied to the housing. This puncture force, which may be any suitable puncture action or technique that maintains (and presumably increases) a force of the blade against the target surface, may drive the blade through the target surface.

As shown in step 1214, when a puncture event occurs, the blade may be released from its locked position. That is, when the axial force on the blade decreases due to puncture of the target surface, the corresponding forces that frictionally engage the blade within the housing are concurrently released so that the blade is free to slide within the housing. In this state, the bias in the spring or other biasing mechanism can withdraw the blade into the retracted position. A similar effect may be achieved by simply removing the blade from the target surface, which would also remove the force against the blade, release the locking mechanism, and cause the spring to retract the blade into the housing. In order to resume the procedure from this state, the blade can once again be deployed with a deployment force as described in step 1202 and the method 1200 may be repeated.

Figure 13:
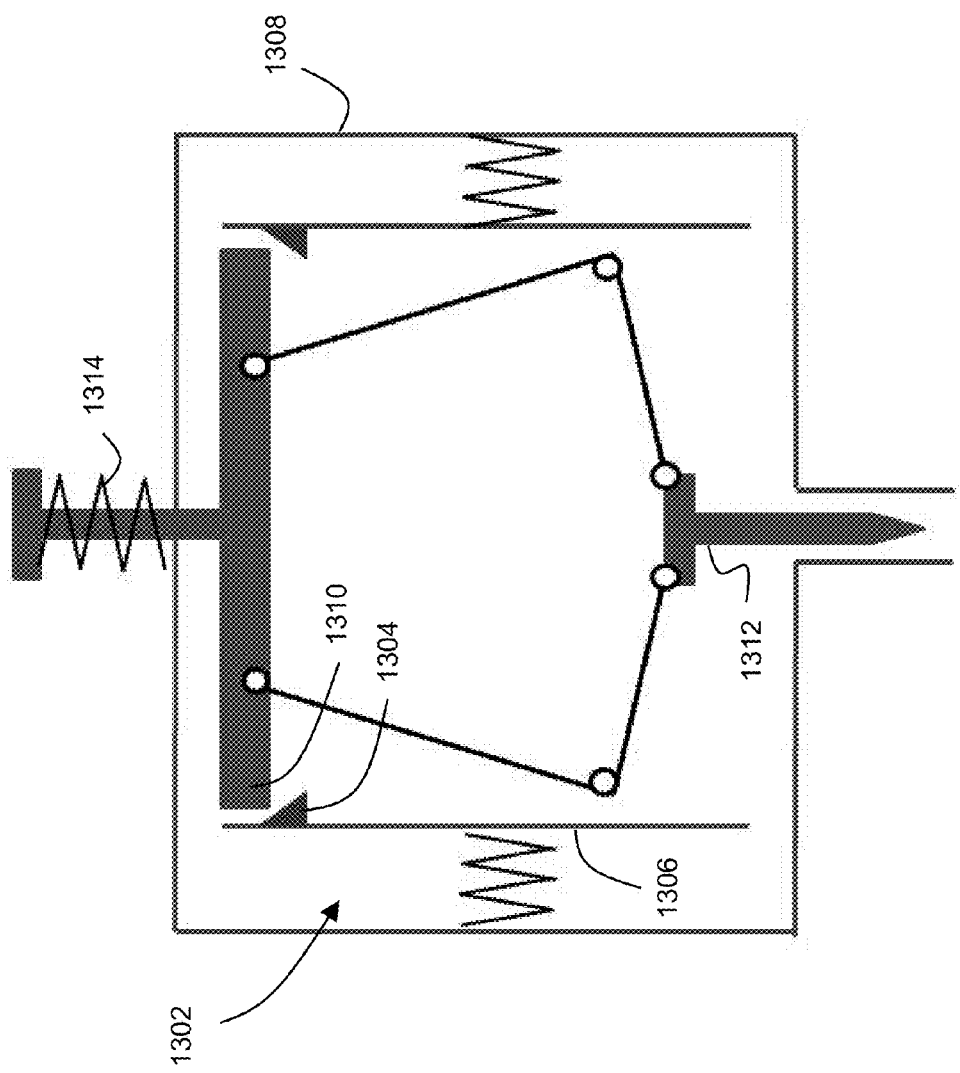
FIG. 13 is a functional diagram of a puncture device with a preload lock.

FIG. 13 is a functional diagram of a puncture device with a preload lock. In general, the preload lock 1302 may include an engagement feature 1304 such as a flange, notch, or hook, clasp, or beveled surface on a compliance structure 1306 such as a cantilevered arm that permits the engagement feature 1304 to move laterally within a housing 1308 into and out of engagement with a corresponding engagement feature 1310 of an instrument 1312 that moves within the housing 1308. In general operation, the engagement feature 1304 is positioned to engage and secure the corresponding engagement feature 1310 of the instrument 1312 when the instrument 1312 is in a deployed position extending from the housing. In this deployed state, the biasing force of a spring or other biasing mechanism 1314 can retain a preloading force that, when released as discussed below, will tend to retract the instrument 1312 from its deployed position and back into an undeployed position (as generally depicted in FIG. 13) with the instrument 1312 disposed within the housing 1308.

Figure 14:
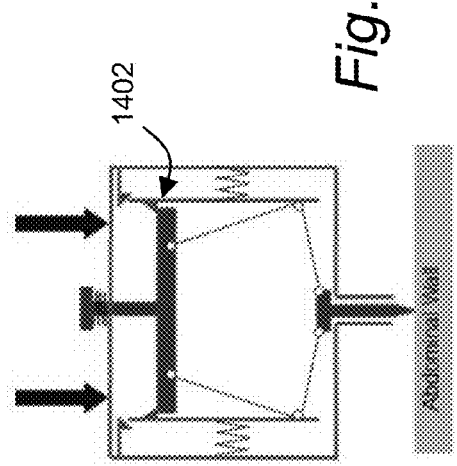
FIG. 14 illustrates a step in a puncture operation.

FIG. 14 illustrates a step in a puncture operation. In FIG. 14, a deployment force has been applied to extend an instrument outside of a housing. A preload lock 1402 is engaged to secure the instrument in the deployed position.

Figure 15:
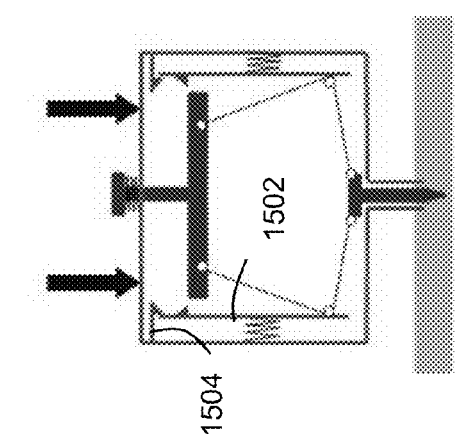
FIG. 15 illustrates a step in a puncture operation.

FIG. 15 illustrates a step in a puncture operation. In FIG. 15, the instrument is partially through a target surface such as an abdominal wall of a patient. An axial force on an instrument laterally displaces an interior surface 1502 of the housing, such as a cantilevered arm or other compliant mechanism. This lateral displacement results from an outward force from the locking mechanism of the instrument that converts the axial force on the instrument to a force that is substantially normal to the interior surface 1502, which latter force frictionally engages the instrument against the interior surface 1502 to secure the instrument in place during a puncture operation. At substantially the same time, the lateral displacement can release the preload lock by moving an engagement feature on the interior surface away from a corresponding engagement feature of the instrument, or more generally, any plunger or other activation mechanism coupled to or otherwise integrated with the instrument.

It will be appreciated that the normal force created against the interior surface 1502 need not be an exclusively normal force. Rather, as used in this context, "substantially normal" is intended to mean having a sufficiently great normal component to frictionally engaged the instrument in a deployed position with enough tenacity to secure the instrument against axial movement into the housing when a contrary puncture force is applied to the housing in a puncture operation. In general, a range of contact angles for the locking arms of the instrument against the interior surface 1502 may provide sufficient normal force, although a more normal contact angle will in general provide a greater normal contact force, and in practice a substantially normal, or slightly less than normal (as illustrated in FIG. 15) contact angle will provide satisfactory results.

The interior surface may further include a preload lock clearing mechanism 1504. This may for example include a spring loaded or compliance driven latch or hook that secures the engagement feature of the preload lock, e.g., on a cantilevered arm as depicted, laterally away from the corresponding engagement feature of the instrument. When the locking mechanism for the blade applies a normal force, e.g., to the cantilevered arm, this may laterally displace the cantilevered arm until the preload lock is secured by the preload lock clearing mechanism 1504. In this manner, the preload lock is held out of the way of the instrument and a return path for the instrument into the housing, thus removing or reducing any timing requirements for the preload lock relative to the locking mechanism when an axial force is removed.

Figure 16:
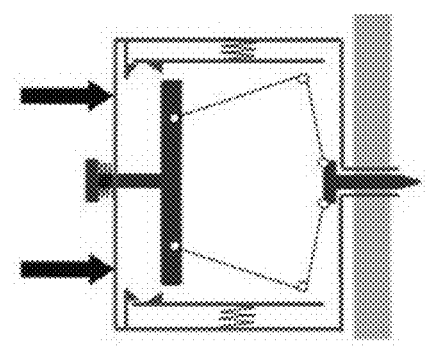
FIG. 16 illustrates a step in a puncture operation.

FIG. 16 illustrates a step in a puncture operation. In FIG. 16, a puncture is completed, thus releasing the axial force on the instrument. This in turn releases the normal forces applied by the blade locking mechanism so that the only force acting on the instrument is the spring bias for the preloaded biasing mechanism.

Figure 17:
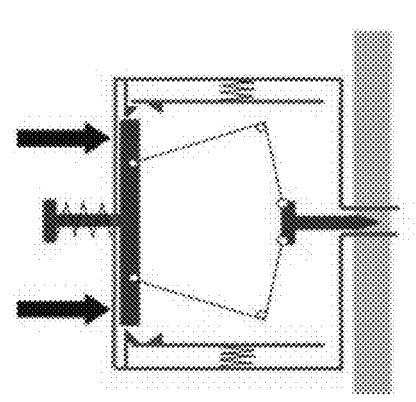
FIG. 17 illustrates a step in a puncture operation.

FIG. 17 illustrates a step in a puncture operation. As shown in FIG. 17, with the axial load removed and the locking mechanism released, the instrument may return into the housing in response to the retraction force applied by the biasing mechanism, e.g., a coil spring or the like.

Figure 18:
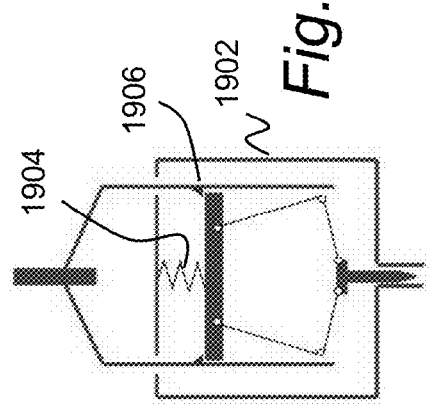
FIG. 18 is a functional diagram of a barrel-loading puncture device.

FIG. 18 is a functional diagram of a barrel-loading puncture device. In general, the device 1800 may provide a locking and preload locking system as contemplated above. However, the device 1800 is generally adapted for use with a drill or other tool that cannot (or generally is not) axially manipulated during use. In order to facilitate preloading and use, an outside barrel is provided that can be operated in pump-action fashion to bias a retraction biasing mechanism and move a cutting instrument into a deployed and preloaded state. A first end 1802 of the device may, for example, be shaped and sized for use in a chuck of a drill, and the housing 1804 may be a cylindrical housing constructed about the internal components and slideably coupled to the instrument 1806, which may for example be a drill bit or other rotary cutting instrument.

Figure 19:
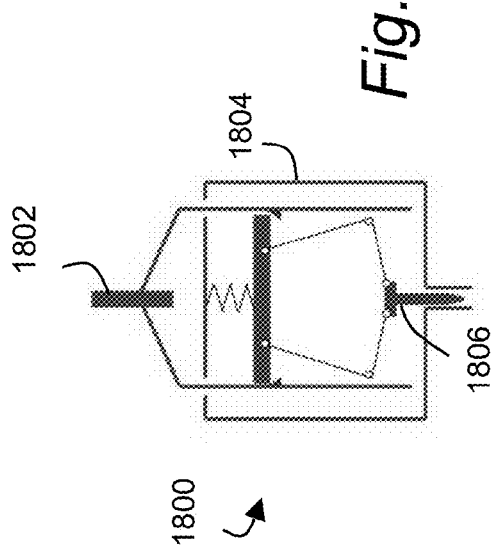
FIG. 19 illustrates operation of a barrel-loading puncture device.

FIG. 19 illustrates operation of a barrel-loading puncture device. By grasping and moving the barrel 1902 of the housing axially forward (downward in the orientation of FIG. 19, as indicated by an arrow 1903), a biasing mechanism 1904, e.g., a spring, can be loaded, and the instrument can be secured against the resulting biasing force with a preload lock 1906 such as any of the preload locks described above. In the configuration of FIGS. 18-21, the cantilevered arms for the instrument locking mechanism and the preload lock extend from the end of the housing distal to the functional tip of the instrument. This permits the exterior of the barrel to move without (necessarily) shifting the various components of the locking mechanisms relative to one another.

Figure 20:
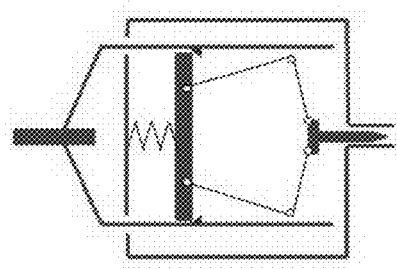
FIG. 20 illustrates operation of a barrel-loading puncture device.

FIG. 20 illustrates operation of a barrel-loading puncture device. With the preload lock engaged, the instrument may in general be secured against axial movement. The housing may then be moved toward a first end 2002 of the device to expose the instrument while the housing moves. When an axial force is applied to the instrument, e.g., when the exposed drill bit is placed against a surface for use, the locking mechanism may be expanded against the interior surface(s) of the housing, e.g., the cantilevered arms. This force can laterally displace the cantilevered arms to release the preload lock, thus preparing the instrument to retract when the axial force is released.

Figure 21:
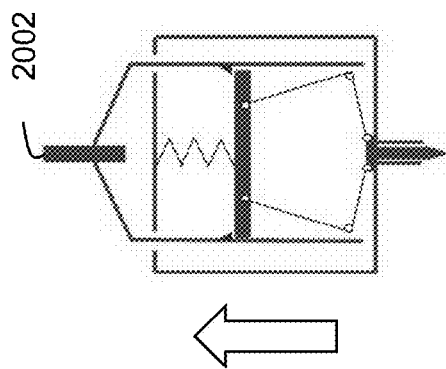
FIG. 21 illustrates operation of a barrel-loading puncture device.

FIG. 21 illustrates operation of a barrel-loading puncture device. As illustrated, when the axial force is released from the instrument, e.g., when a puncture event occurs, the instrument may retract into the housing under force from the biasing mechanism.

It will be understood that numerous adaptations may be made for use in rotary tools. For example, while complementary left and right locking mechanisms are depicted, the device may use any number of radially distributed preload locks and locking mechanisms. Further, the device may use a different number of preload locks and locking mechanisms, provided that the resulting configuration permits the preload locks to be released substantially at the same time that the locking mechanism engages. It will also be understood that drills may rotate at hundreds or thousands of revolutions per minute, creating significant centripetal forces on various compliance features such as cantilevered arms or springs. A variety of techniques may be employed to account for such rotationally induced forces so that the device remains locked when axially loaded and becomes released when the axial load is removed. In another aspect, the axial locking mechanism and/or preload lock may be mechanically isolated from the drill-to-drill bit coupling, e.g., with one or more thrust bearings and axial sliders, to permit rotational isolation of the locking mechanisms from the drill.

Figure 22:
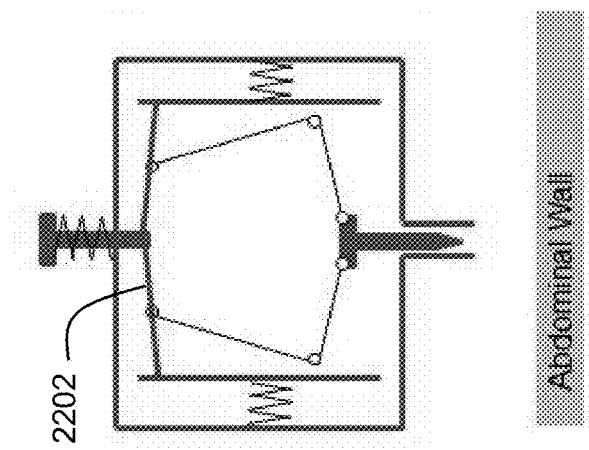
FIG. 22 illustrates a puncture device with a bistable preload lock.

FIG. 22 illustrates a puncture device with a bistable preload lock. In general, a bistable mechanism 2202 may have two stable states under axial loading, and a center state where two opposing arms are collinear. When a force is applied, e.g., to a plunger, the bistable mechanism 2202 may pass through the center state and then drive an instrument out of the housing to a deployed position.

Figure 23:
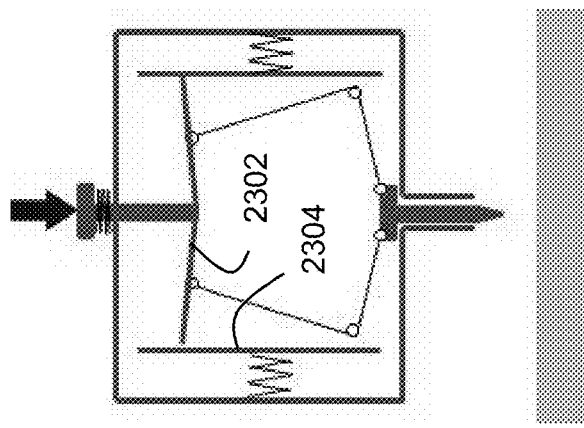
FIG. 23 illustrates a puncture device with a bistable preload lock.

FIG. 23 illustrates a puncture device with a bistable preload lock. With the instrument deployed, the bistable mechanism 2302 may, upon a return path induced by a biasing mechanism, frictionally engage an interior surface 2304 of a housing, such as the cantilevered arms described above. In this state, the biasing force is converted into substantially normal forces by the arms of the bistable mechanism against the interior surface 2304 of the housing, thus locking the instrument in a preloaded state with the instrument deployed and a biasing return force retained by the preload lock.

Figure 24:
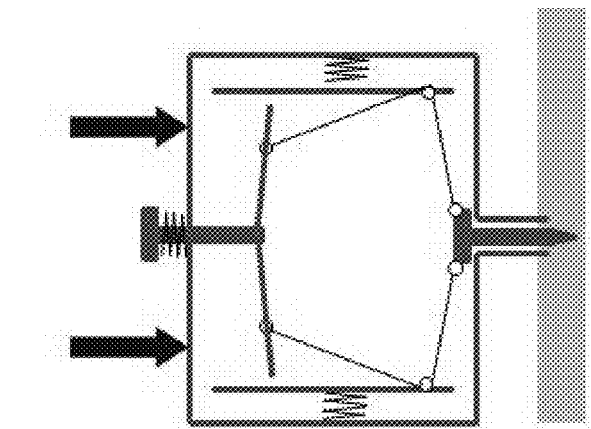
FIG. 24 illustrates a puncture device with a bistable preload lock.

FIG. 24 illustrates a puncture device with a bistable preload lock. As illustrated, when an axial load is applied to the deployed instrument, a locking mechanism displaces the interior surface of the housing to lock the instrument in a deployed position. This lateral displacement of the interior surface may also release the axial loading on the bistable preload lock, thus permitting the preload lock to move to a second bistable state where the bistable preload lock can move axially upward within the housing.

FIG. 25 illustrates a puncture device with a preload lock. The device 2500 may advantageously be constructed from a small number of parts using a variety of techniques. For example, a functional interior surface may be provided by one or more cantilevered arms 2502 integrated into the housing 2504.

In one aspect, the instrument 2506 may include one or more notches 2508 or the like to receive one or more corresponding arms 2510 of a plunger 2512. This arrangement may provide certain structural advantages such as permitting the arms 2510 to pivot within the notches 2508, while securely coupling the plunger 2512 to the instrument 2506 against axial displacement.

FIG. 26 illustrates the puncture device of FIG. 25 in a preloaded state. In particular, one or more engagement features of the plunger are secured to corresponding engagement features of the cantilevered arms within the housing. In this secure relationship, the bias on a spring 2602 or the like can be maintained for use in retracting the instrument after a puncture event.

Figure 27:
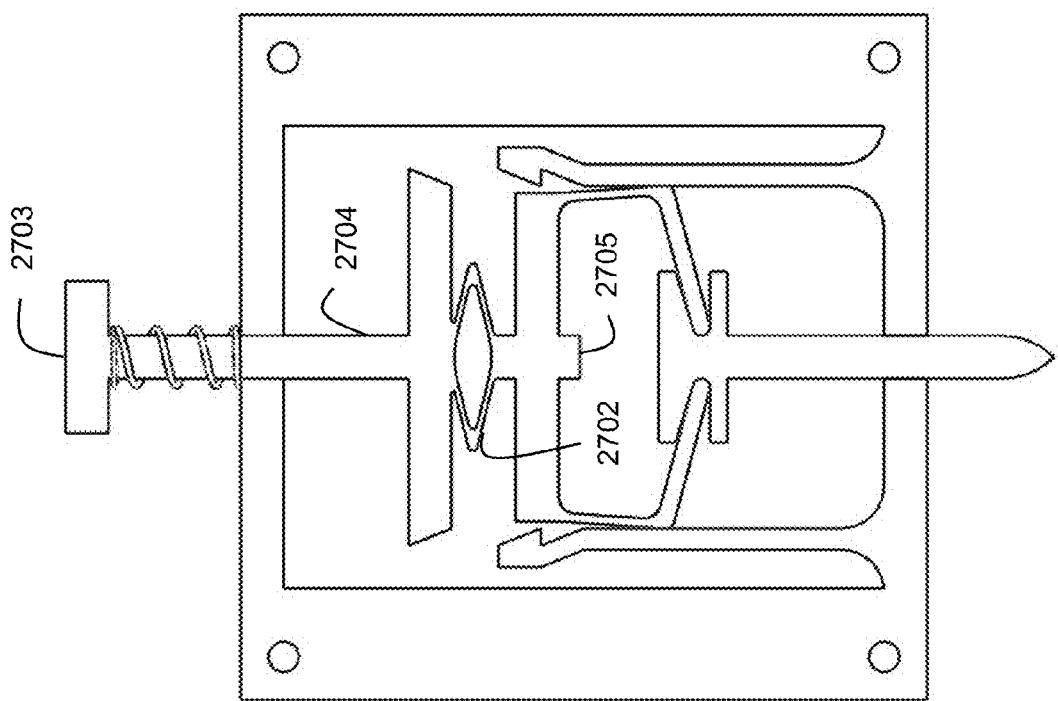
FIG. 27 illustrates a puncture device with a compliance mechanism.

FIG. 27 illustrates a puncture device with a compliance mechanism for a preload lock. The compliance mechanism 2702 may, for example, be integrated into the plunger 2704, and may include any other spring(s) or other biasing mechanism(s) that are flexible, but tend to bias a first end 2703 of the plunger 2704 to move to a predetermined distance from a second end 2705 of the plunger 2704. The compliance mechanism 2702 can effectively spring-load the preload lock so that when the preload lock is released—that is, when an axial load is applied to the deployed instrument—the engagement features of the preload lock can spring axially away from corresponding engagement features of the interior of the housing. This configuration can advantageously reduce the chances of the preload lock re-engaging. For example, where there is some latency between release of the locking mechanism for the instrument and axial movement due to the preload bias, the cantilevered arms or other interior surfaces may move to an unloaded position where the preload lock is intended to engage. By moving the engagement features of the preload lock axially away from one another immediately upon release of the preload lock, any resulting, unintended engagement with the preload lock can be avoided.

It will also be noted that where cantilevered arms are used, the cantilevered arms may include one or more relief features such as notches as illustrated to preferentially engage an instrument locking mechanism at one or more locations. This may include functional engagement such as axial locking of the instrument for a puncture operation, or to provide tactile feedback to a user concerning state changes such as initial movement of a plunger or preload locking.

It will be understood that while a flexural compliance mechanism is illustrated, axial compliance sufficient to separate preload lock engagement features may be achieved with a variety of compliance techniques including without limitation any spring, flexural element, resilient material and the like, as well as combinations of the foregoing.

Other techniques may also or instead be used to prevent the preload lock from reengaging when the locking mechanism for a functional tip is released. For example, a viscoelastic damper such as a foam or similar material may couple the cantilevered arms to the interior walls of the housing, or the cantilevered arms may be wholly or partially formed of a viscoelastic material that returns slowly to an unloaded state. In this manner, the cantilevered arms or any similar structure can be fabricated in a manner that will not snap quickly back into an undeformed shape, e.g., where the preload lock engagement features might prevent axial movement of the instrument within the housing.

Figure 28:
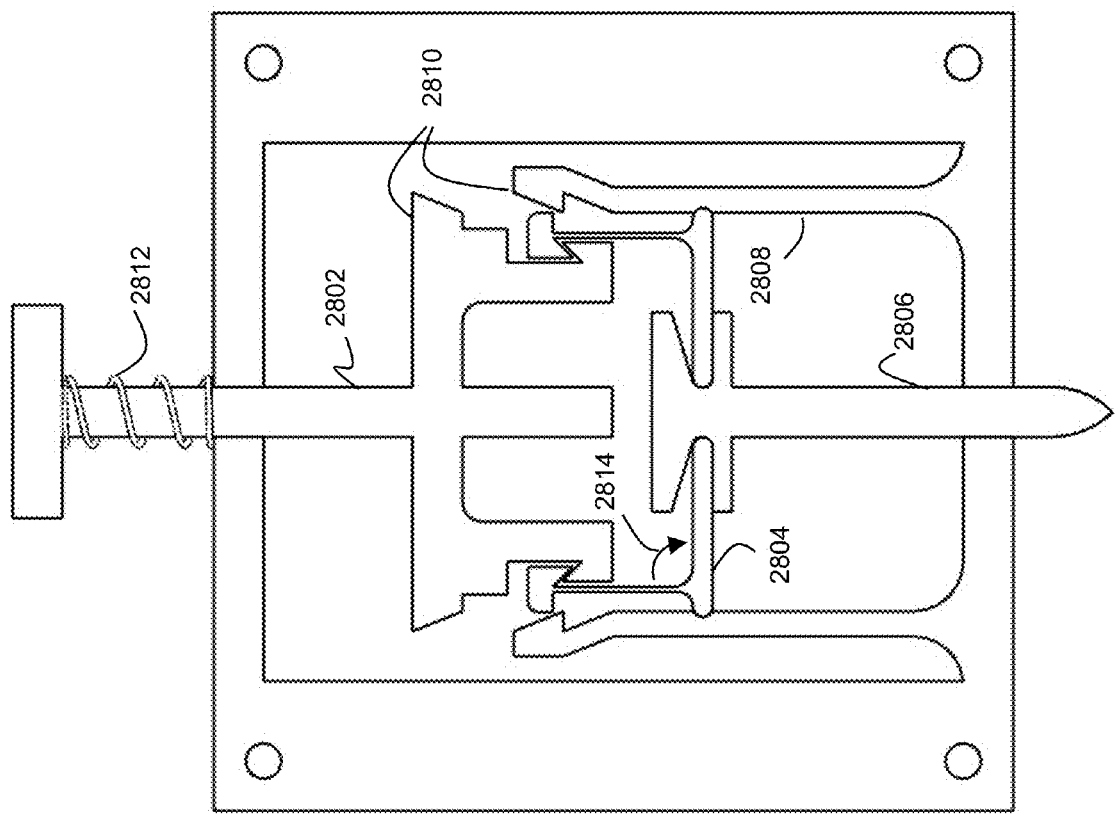
FIG. 28 illustrates a puncture device with a compliance mechanism.

FIG. 28 illustrates a puncture device with a compliance mechanism. As shown in the drawing, when an instrument is locked in a deployed position by an axial load, a spring bias to clear the preload lock may be provided by the same biasing mechanism that provides the force to retract the instrument after a puncture event. The plunger and locking mechanism may be fabricated as a three-part assembly with a first part 2802, a second part 2804 and a third part 2806 (rigidly coupled to an instrument). In this configuration, the first part 2802, which is coupled to a plunger, can move relative to the second part 2804 and the third part 2806. When the cantilevered arms 2808 are laterally displaced such that the preload locking features 2810 are not engaged, the first part 2802 can move axially due to the force of the biasing mechanism 2812 so that the respective features are moved axially out of alignment as illustrated. In this state, there is no opportunity for the preload locking features 2810 to engage around the time when a locking mechanism for the instrument is released.

It will also be noted that the second part 2804 includes arms that rest in corresponding notches of the third part 2806. This permits the arms to rotate as indicated by an arrow 2814 so that when the instrument is deployed and an axial force is applied to the instrument, the arms will tend to laterally displace the cantilevered arms as increasing axial force is applied to provide a locking mechanism as described above.

Figure 29:
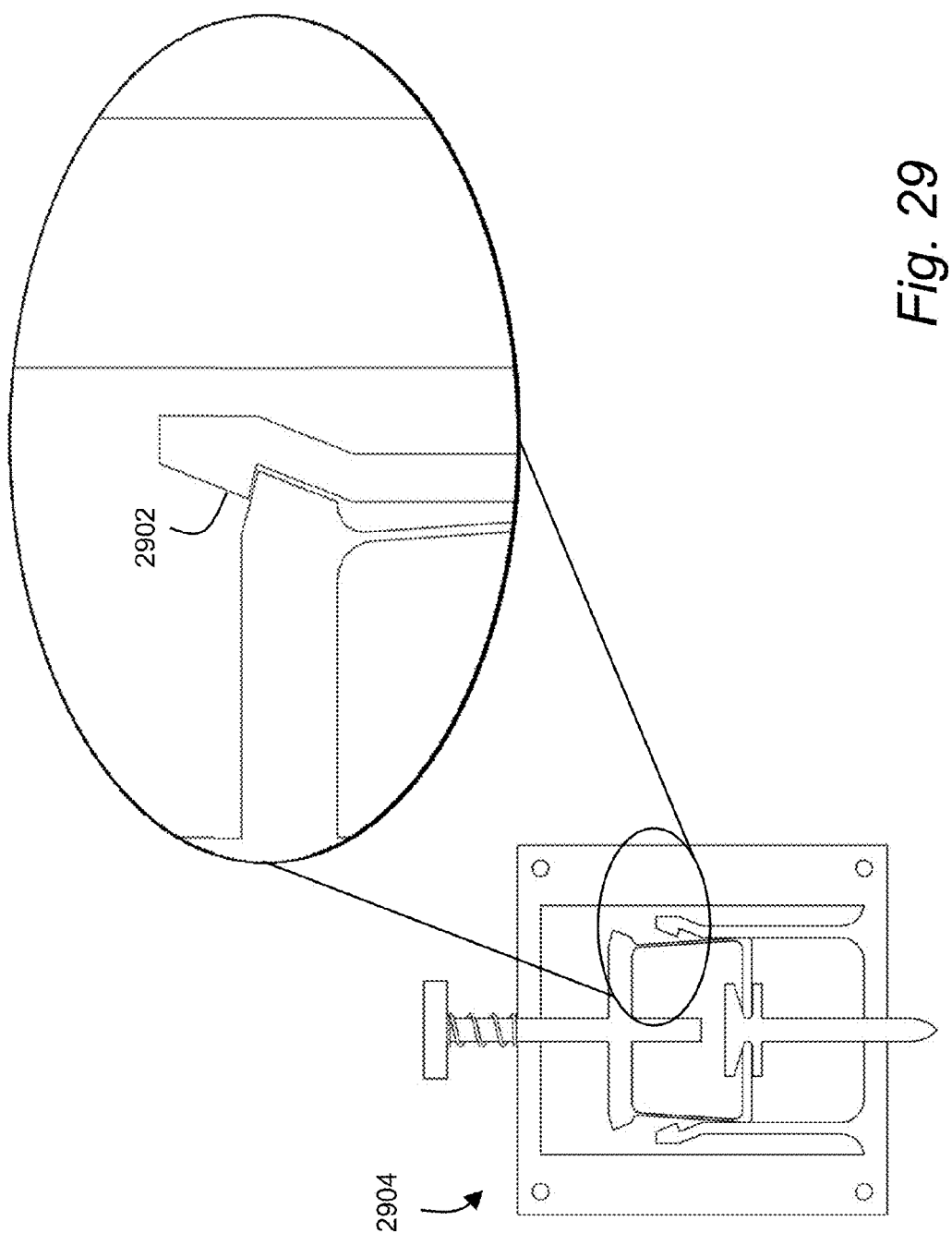
FIG. 29 illustrates a puncture device with an angled preload locking mechanism.

FIG. 29 shows a puncture device with an angled preload locking mechanism. The preload locking mechanism 2902 of the puncture device 2904 is shown in an expanded view 2906 in an engaged state. In general, when an instrument is deployed, the movement of components within the puncture device 2902 may apply normal forces to one or more cantilevered arms to laterally displace the arms. This tends to move the cantilevered arms out of alignment with the primary axis of the puncture device 2904, and diminishes the effectiveness of preload locking mechanisms that rely on normal contact forces for frictional engagement. In order to mitigate this effect, the preload locking engagement features may be pre-angled as illustrated in the figure so that they are substantially parallel to one another when locked in the preloaded stated. It will be understood that the actual angle will depend on the amount of deflection in the cantilevered arm, and may vary significantly from design to design. Thus the angled preload locking features depicted in FIG. 29 are by way of example only, and should in general be understood to include any angle or angles that maintain substantially parallel surfaces for complementary engagement features, or more generally any angle that improves the tenacity of engagement between such complementary engagement features.

The method steps of the invention(s) described herein are intended to include any suitable method of causing such method steps to be performed, consistent with the patentability of the following claims, unless a different meaning is expressly provided or otherwise clear from the context. So for example performing the step of X includes any suitable method for causing another party, device, or system, such as a remote user or a remote processing resource (e.g., a server or cloud computer) to perform the step of X. Similarly, performing steps X, Y and Z may include any method of directing or controlling any combination of such other individuals, devices, systems or other resources to perform steps X, Y and Z to obtain the benefit of such steps.

It will be appreciated that the methods and systems described above are set forth by way of example and not of limitation. Numerous variations, additions, omissions, and other modifications will be apparent to one of ordinary skill in the art. While particular embodiments of the present invention have been shown and described, it will be apparent to those skilled in the art that various changes and modifications in form and details may be made without departing from the spirit and scope of the invention as defined by the following claims. The claims that follow are intended to include all such variations and modifications that might fall within their scope, and should be interpreted in the broadest sense allowable by law.

What is claimed is:

1. A device comprising:
    a housing having an axis;
    an instrument slidably retained within the housing and movable along the axis between a first position wherein a functional tip of the instrument extends outside the housing and a second position wherein the functional tip is disposed within the housing;
    a biasing mechanism that biases the instrument toward the second position;
    a preload lock with one or more features that secure the instrument in the first position against movement by the biasing mechanism; and
    a locking mechanism that releases the preload lock and secures the instrument against moving from the first position to the second position by frictionally engaging an interior wall of the housing with a force proportional to a load applied to the functional tip in a direction from the first position to the second position along the axis of the housing.

2. The device of claim 1 wherein the functional tip includes a cutting edge.

3. The device of claim 1 further comprising a plunger coupled to the instrument to permit movement of the instrument between the first position and the second position.

4. The device of claim 3 wherein the plunger is operable at a first end of the housing distal from a second end of the housing where the functional tip of the instrument extends outside the housing.

5. The device of claim 4 wherein the biasing mechanism includes a coil spring about the axis and coupled to the plunger and the housing.

6. The device of claim 1 wherein the locking mechanism includes:
    a mechanical member that converts an axial force on the functional tip to a normal force; and
    an interior surface of the housing substantially parallel to the axis and positioned to receive the normal force of the mechanical member, thereby frictionally engaging the functional tip against axial movement due to the axial force.

7. The device of claim 6 wherein the interior surface includes a cantilevered arm.

8. The device of claim 7 wherein the preload lock includes an engagement feature on the cantilevered arm positioned to secure a corresponding engagement feature of the instrument when the instrument is in the first position.

9. The device of claim 8 wherein the normal force laterally displaces the cantilevered arm to release the preload lock.

10. The device of claim 1 wherein the functional tip is a surgical cutting instrument.

11. The device of claim 1 wherein the functional tip is a drill.

12. The device of claim 1 wherein the instrument includes a compliance mechanism that axially biases the one or more features of the preload lock away from one or more corresponding engagement features of the housing when the preload lock is released.

13. The device of claim 1 wherein the instrument includes a viscoelastic damper to prevent the preload lock from reengaging when the locking mechanism for the functional tip is released.

14. A method comprising:
    applying a deployment force to spring load a blade in a deployed position exposed outside a housing with a bias force to return to a retracted position within the housing;
    locking the blade with a preload locking force in the deployed position against the bias force;
    releasing the deployment force;
    pressing the blade against a target surface while in the deployed position, thereby creating a force against the blade; and
    converting the force against the blade into a first force to release the preload locking force and a second force normal to an interior surface of the housing to establish a friction fit against the interior surface proportional to the force against the blade.

15. The method of claim 14 further comprising applying a puncture force to the housing to drive the blade through the target surface, thereby releasing the force against the blade and the friction fit against the interior surface and causing the bias to retract the blade into the retracted position.

* * * * *